United States Patent
Dolinsky et al.

(10) Patent No.: US 9,529,097 B1
(45) Date of Patent: Dec. 27, 2016

(54) PIXELATED GAMMA DETECTOR

(71) Applicant: General Electric Company, Schenectady, NY (US)

(72) Inventors: Sergei Ivanovich Dolinsky, Clifton Park, NY (US); Brian David Yanoff, Niskayuna, NY (US); Renato Guida, Wynantskill, NY (US); Adrian Ivan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 15/198,502

(22) Filed: Jun. 30, 2016

(51) Int. Cl.
*G01T 1/202* (2006.01)
*G01T 1/20* (2006.01)
*G01T 1/164* (2006.01)

(52) U.S. Cl.
CPC .............. *G01T 1/202* (2013.01); *G01T 1/1644* (2013.01); *G01T 1/2002* (2013.01); *G01T 1/2018* (2013.01); *G01N 2223/053* (2013.01); *G01N 2223/41* (2013.01); *G01N 2223/505* (2013.01); *G01N 2223/628* (2013.01); *G01N 2223/646* (2013.01)

(58) Field of Classification Search
CPC ...... G01T 1/202; G01T 1/2002; G01T 1/2018; G01T 1/1644
See application file for complete search history.

(56) References Cited

U.S. PATENT DOCUMENTS

| | | | |
|---|---|---|---|
| 4,394,576 A | 7/1983 | Tanaka et al. | |
| 6,462,341 B1 | 10/2002 | Muchllehner | |
| 6,710,349 B2 | 3/2004 | Shao | |
| 7,564,948 B2 | 7/2009 | Wraight et al. | |
| 7,569,826 B2 | 8/2009 | Uribe et al. | |
| 8,809,793 B2 | 8/2014 | Wagadarikar et al. | |

(Continued)

OTHER PUBLICATIONS

Spartoris, Konstantinos et al., "A photon counting CdTe gamma- and X-ray camera", Nuclear Instruments and Methods in Physics Research Section A: Accelerators, Spectrometers, Detectors and Associated Equipment, Volume: 550, Issues: 1-2, 2005, pp. 267-277, 11 pp.

(Continued)

*Primary Examiner* — David Porta
*Assistant Examiner* — Mindy Vu
(74) *Attorney, Agent, or Firm* — Joseph J. Christian (57) ABSTRACT

A pixelated gamma detector includes a scintillator column assembly having scintillator crystals and optical transparent elements alternating along a longitudinal axis, a collimator assembly having longitudinal walls separated by collimator septum, the collimator septum spaced apart to form collimator channels, the scintillator column assembly positioned adjacent to the collimator assembly so that the respective ones of the scintillator crystal are positioned adjacent to respective ones of the collimator channels, the respective ones of the optical transparent element are positioned adjacent to respective ones of the collimator septum, and a first photosensor and a second photosensor, the first and the second photosensor each connected to an opposing end of the scintillator column assembly. A system and a method for inspecting and/or detecting defects in an interior of an object are also disclosed.

20 Claims, 4 Drawing Sheets

(56) References Cited

U.S. PATENT DOCUMENTS

| | | | |
|---|---|---|---|
| 2010/0294940 A1* | 11/2010 | Wieczorek | G01T 1/2018 250/363.03 |
| 2014/0030832 A1 | 1/2014 | Selfe et al. | |
| 2014/0353510 A1* | 12/2014 | Spanoudaki | G01T 1/1644 250/362 |
| 2015/0212216 A1* | 7/2015 | Van Zuiden | G01T 1/1648 250/362 |
| 2016/0003741 A1 | 1/2016 | Diebold et al. | |

OTHER PUBLICATIONS

MacLeod et al., "Development of a compton imager based on scintillator bars", Nuclear Science Symposium and Medical Imaging Conference (NSS/MIC), 2011 IEEE, pp. 444-449, 6 pp.

\* cited by examiner

PIXELATED GAMMA DETECTOR

GOVERNMENT SUPPORT

Made using government support provided by the U.S. Department of Energy, National Energy Technology Laboratory under Agreement No. DE-FE0024293.

BACKGROUND

Instrumentation for inspecting the integrity of a borehole casing can use gamma ray sources and gamma detectors. In some implementations, radiation from an x-ray or gamma ray source can be reflected from the casing to determine the casing density, weld quality, voids, etc. Conventional instrumentation can include a probe body containing a gamma ray source and a gamma ray detector separated by a predetermined length. The collected data can represent the response seen at the detector when radiation is passed from the source into the borehole's wall formation. Some radiation will be lost, but some will be scattered and reflect back toward the detectors, this reflected radiation being useful in determining properties of the formation.

DETAILED DESCRIPTION

Embodying devices and methods provide a segmented detector element using a minimal number of photosensors (e.g., photomultiplier tubes (PMT), solid state photomultipliers). An embodying detector element provides radiation detection for a large number of pixels with a minimum number of photosensors, while maintaining a high signal-to-background noise ratio. The embodying detector includes a collimator with multiple holes to get angular and spatial resolution from back-scattered gamma rays off the borehole casing. The detector includes multiple pixels to register radiation detection events.

An embodying detector is expected to be used in environments with elevated temperature of up to 200° C., accordingly direct conversion semiconductor detectors cannot be used. An embodying detector is based on scintillator crystals providing detected radiation event signals to high temperature photosensors, which can operate at these elevated temperatures.

Due to limited space inside the borehole, and/or well, it is not possible for conventional detectors implemented with a PMT to readout individual detector scintillator pixels. Commercially available high temperature PMTs have only a single channel for readout. A detector in accordance with embodiments can provide multiple pixel readouts using two PMTs. Conventional approaches have each scintillator pixel coupled to its own individual PMT and dedicated readout electronics. Because a high temperature PMT is large and bulky, it is unpractical to have a detector with high granularity (multiple PMTs) implementing the conventional approach. Embodying detectors achieve high granularity and multiple detection pixels using only two PMTs, thus providing a practical down-hole detector suitable for high temperature applications.

In accordance with embodiments, a stack of scintillators and optically transparent spacers are assembled to form a detector rod. Opposing ends of the embodying detector rod are coupled to a respective single-channel PMT. For each event, a ratio of signal amplitude from the two respective PMTs can be used to identify a unique scintillator pixel within the detector rod that captured the radiation detection event. An embodying detector can have a lower cost, is less sensitive to background noise, and has better spatial resolution than conventional scintillating rods.

A scintillator radiation detector requires scintillator material to convert radiation quanta to scintillation light, and a photosensor to detect the scintillation light and convert it to an electric signal. In a basic, conventional configuration, one scintillator can be optically coupled to one photosensor. The type, energy, and time-of-detection of the radiation quanta is the only information available from this basic configuration. However, this configuration cannot provide spatial information about the location of the quantum detection event, other than that it occurred inside the sensitive volume of the scintillator.

Many applications (e.g., medical nuclear scanners, high energy physics and/or astrophysics research instrumentation) require a better spatial resolution than the size of the detector. To obtain spatial and positional resolution with a certain accuracy ($\Delta x$), the simple configuration of one scintillator to one photosensor can be replicated as many times as necessary to cover a predetermined radiation field-of-view. In this implementation, the individual scintillator units (pixel) have a size of about $\Delta x$ (the spatial resolution). This conventional approach has an overhead disadvantage of requiring one photosensor device and its associated readout electronic channel per scintillator pixel, which becomes extremely cost- and performance-challenging for large field-of-view applications. Additionally, for high spatial resolution applications, hundreds or thousands of pixels can be required (along with corresponding photosensors and readout electronics).

To reduce this overhead, conventional scintillator radiation detectors are sometimes based on multiple pixelated scintillators coupled to one position-sensitive photosensor to reduce the number of photosensors and electronic channels. The position of the radiation scintillation event can be decoded to the predetermined spatial resolution $\Delta x$ by using controlled light sharing techniques between the pixels.

Another conventional approach to reduce the scintillator-to-photosensor overhead is to use a monolithic scintillator that is optically coupled with two or more photosensors. In this approach, the position of the scintillation event can be decoded by processing information from the photosensors with a position reconstruction algorithm (e.g., a center-of-gravity calculation). By way of example for this approach, a long scintillator crystal can be optically coupled with two photosensors located at ends of the crystal. A simple algorithm using signals received from the first photosensor (TopPhS), and the second photosensor (BottomPhS) can calculate the relative position x of the radiation scintillation event along the long axis of the detector rod (e.g., x=(TopPhS-BottomPhS)/(TopPhS+BottomPhS)).

To determine the direction of the radiation incident on the detector, some conventional detectors add additional collimating structures to shape the incident radiation flux. These collimator structures can be made of a radiation absorbent/blocking material (e.g., tungsten, lead, etc.). Channels, or holes, are left exposed to the radiation in the field-of-view to allow determination of the direction of radiation striking the detector from measured position of scintillation event. Conventional collimators (typically used in nuclear medicine single-photon emission computed tomography (SPECT) systems) include a parallel-hole collimator, a pinhole collimator (that can produce a magnified image of a small object of interest), and converging collimators (that can also magnify the object).

Collimators can be used for pixelated, as well as monolithic, scintillator detectors. In conventional detector systems with collimators, the whole volume of scintillator material is sensitive to the radiation quanta that penetrate the collimator septa. Also, radiation can reach the scintillator material at angles outside the field-of-view blocked by the collimator absorbers. These extraneous signals reaching the scintillator represent a source of background noise in the measurement. In addition, certain back-scattering systems make use of high-activity radiation sources, where the collimators and source shielding can be subject to significant penetrability of radiation photons arriving from unwanted directions, or source locations, outside of the predetermined field-of-view.

In accordance with embodiments, a pixelated gamma detector is provided where the number of pixels is greater than the number of photosensors. An embodying detector can be used in applications where the design requirements determine a collimator geometry projecting radiation only onto a small fraction of scintillator volume, while satisfying the required spatial resolution $\Delta x$.

Embodying detectors have an advantage in backscattering systems applications using high-activity radiation sources by reducing the sensitivity of those portions of the detector exposed to background radiation photons. This preserves the measurement signal/noise ratio and reduces the count rates below the system processing bandwidth. In accordance with embodiments, regions of scintillator outside the field-of-view are replaced with radiation-insensitive material, which can still allow the scintillation light to travel to the photosensors for position reconstruction and energy measurement.

Figure 1:
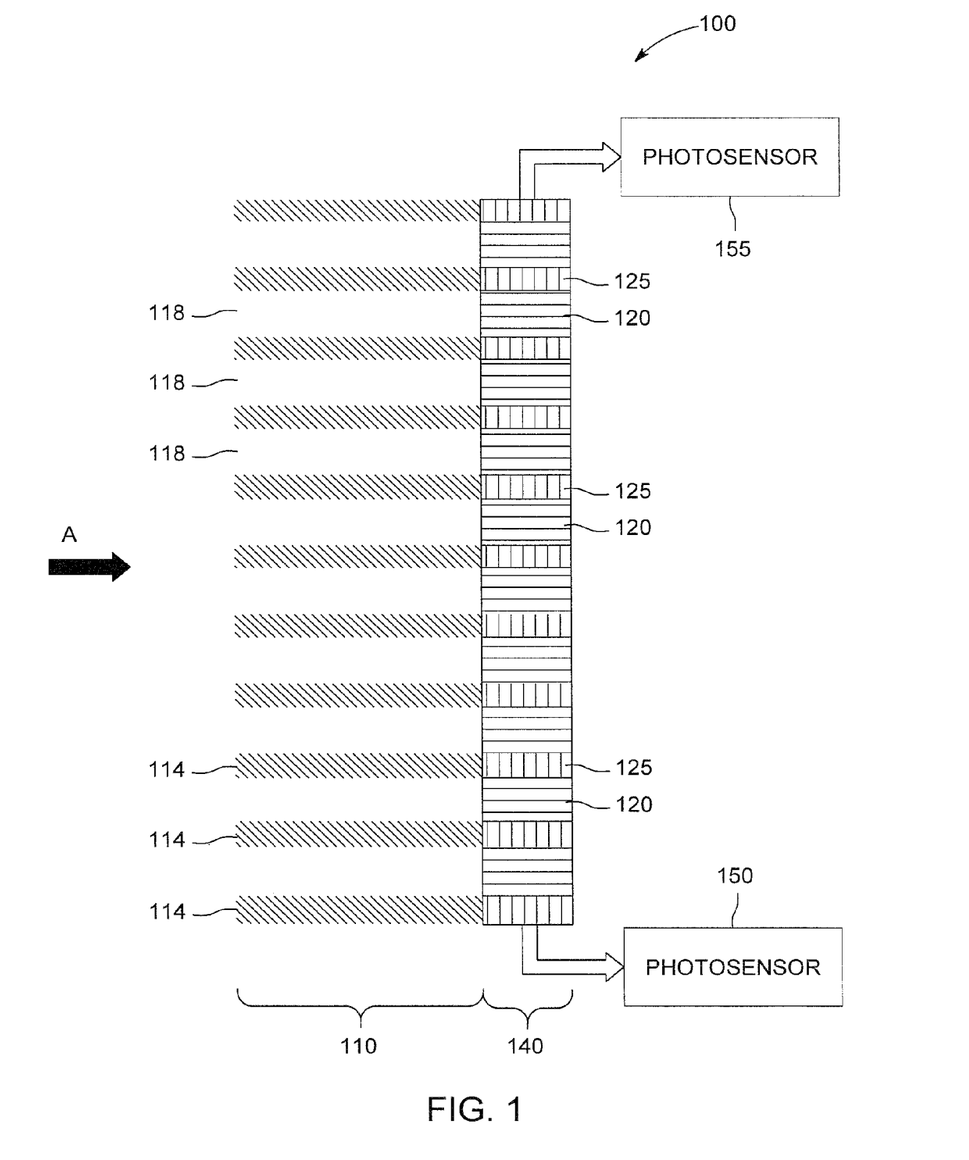
FIG. 1 schematically depicts a cross sectional view of a pixelated gamma detector in accordance with embodiments.

FIG. 1 schematically depicts a sectional view of pixelated gamma detector 100 in accordance with embodiments. Pixelated gamma detector 100 includes collimator 110 having about parallel longitudinal walls (not shown) separated by about parallel collimator septum 114, where two collimator septa define a respective collimator channel 118 between the two septa and the longitudinal walls. Scintillator crystals 120 are positioned abutting the collimator channel—i.e., not in the shadow of the collimator septa. The scintillator crystals can be made from Sodium Iodide: Thallium (NaI:Tl), Lutetium Yttrium Oxy-orthosilicate (LYSO), or other radiation responsive crystal. For purposes of this discussion, arrow A depicts the direction of the backscatter radiation incident on the pixelated gamma detector.

Optical transparent elements 125 alternate with the scintillator crystals and are located in regions that are shadowed by the collimator septum. These optical transparent elements do not emit scintillation light under incident radiation. Thus, unlike with conventional detectors, unwanted background radiation is not detected in the collimator septum shadow regions because optical transparent elements 125 are not sensitive to the radiation quanta that penetrates the collimator septa. The optical transparent elements can be made from material that is inert for scintillation under radiation—e.g., glass, acrylic, optical epoxy, etc.). In accordance with embodiments, respective ones of optical transparent elements 125 can have a different directional optical reflectivity property to control light distribution within scintillator column assembly 140.

FIG. 1 depicts a pixelated gamma detector having a detector stack of ten scintillator pixels. It should be readily understood that embodying pixelated gamma detectors can have fewer, or greater, scintillator pixels.

Because scintillator column assembly 140 is optically transparent, the scintillation light generated by scintillator crystals 120 can propagate through the column assembly to photosensors 150, 155. The photosensors are connected to scintillator column assembly 140 at opposing ends of the column. The photosensors convert the light photons from the scintillator column assembly to electrical pulses. The timing and amplitude of the electrical pulses can be processed to give information about the location (e.g., relative position x) of the radiation interaction, and the energy deposited in the scintillator as described above.

Figure 2:
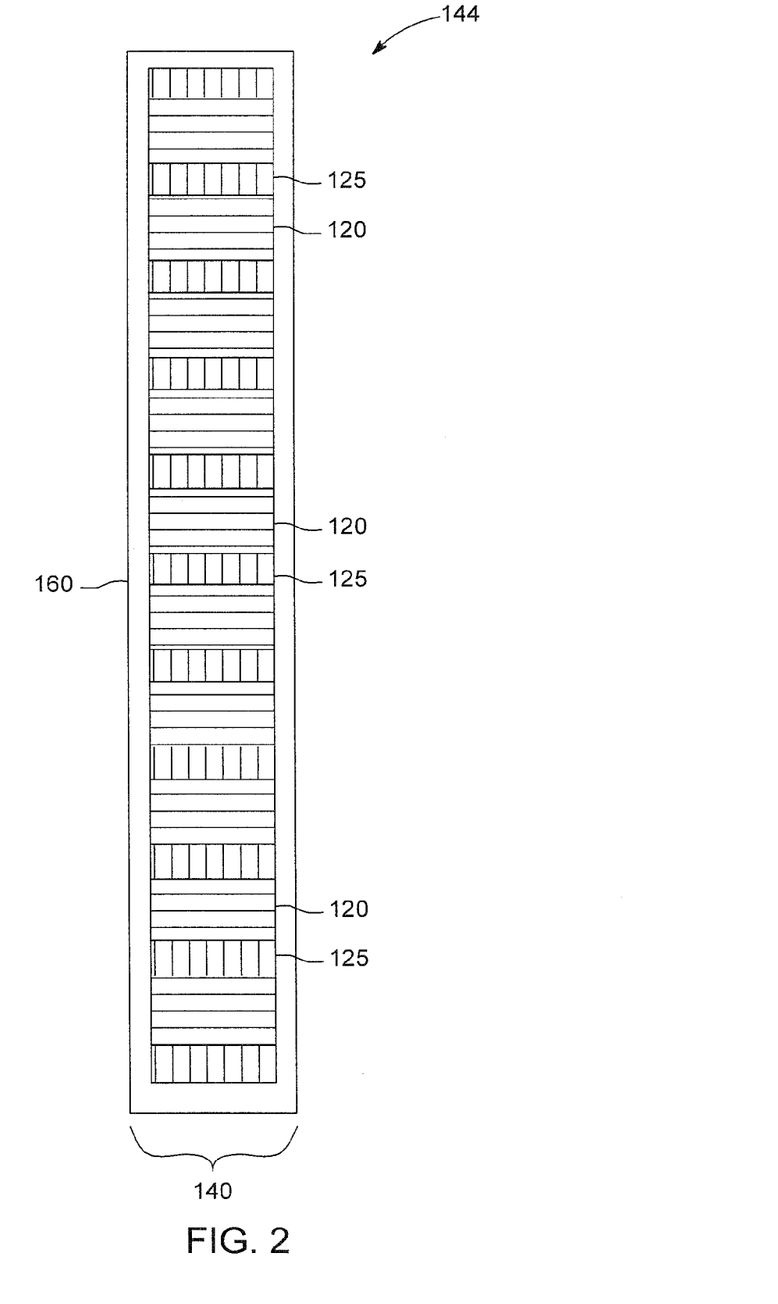
FIG. 2 schematically depicts a cross sectional view of an encased scintillator column assembly in accordance with embodiments.

FIG. 2 schematically depicts cross sectional view of encased scintillator column assembly 144 in accordance with embodiments. Encased scintillator column assembly 144 includes scintillator column assembly 140 (formed from alternating scintillator crystals 120 with optical transparent elements 125 as disclosed above) encased in optical transparent casing 160. In accordance with embodiments, optical transparent casing 160 can be formed from clear quartz fused along abutting edges to encase optical column assembly 140. However, other optically transparent materials used in different optical applications as light guides can be substituted to encapsulate scintillator column assembly 140 (e.g., glass, optically transparent epoxy, optical liquid, air or other gas, etc.). In accordance with embodiments, any gaps between an inner surface of the optical transparent casing and scintillator column assembly can be filled with an optical epoxy.

Figure 3:
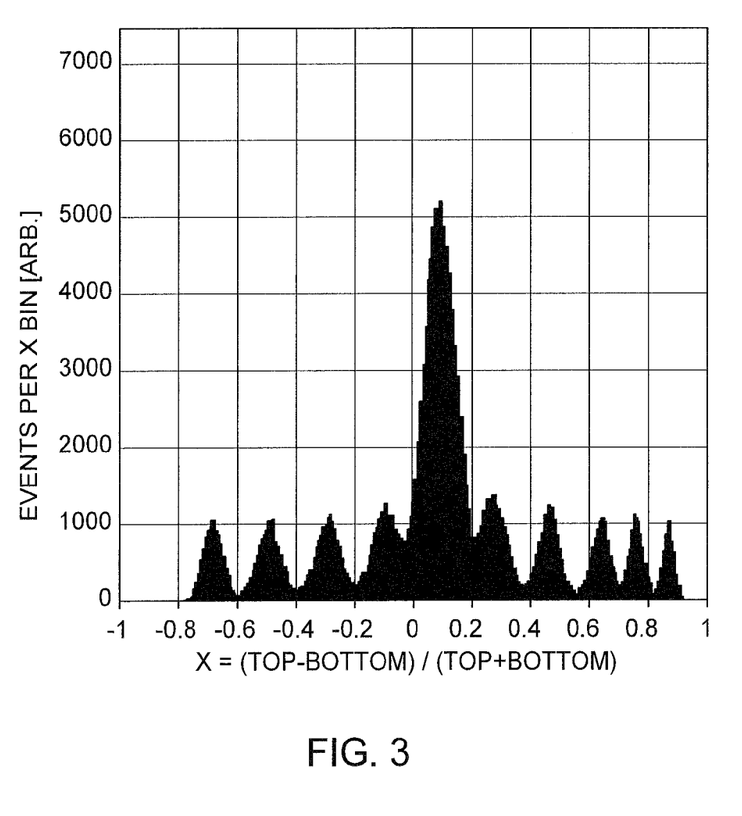
FIG. 3 graphically depicts performance of a pixelated gamma detector in accordance with embodiments.

FIG. 3 graphically depicts performance of pixelated gamma detector 100 in accordance with embodiments. The graph illustrates count rate (vertical axis) versus the reconstructed relative position x along the detector rod (horizontal axis). Measurements were taken using a proof-of-concept embodying pixelated detector. The data depicted is for a pencil beam (simulating the backscatter radiation) positioned to illuminate the fifth pixel in the stack of ten pixels. Note that because the scintillator crystals in this proof-of-concept prototype are formed from LYSO, which contains the radioisotope $^{176}$Lu, nine small peaks are present in the signal. These nine small peaks are from the other nine pixels because of the self-background characteristics of LYSO. Implementations of scintillator crystals from other materials free of self-background (e.g., NaI:Tl, Bismuth germanium oxide (BGO), gadolinium pyrosilicate (GPS), etc.) would not have these small peaks.

In accordance with embodiments, a pixelated gamma detector can be formed from pixelated scintillators encased in optically transparent media, where the active pixels are aligned with collimator channels, and separated by optically transparent material aligned with the collimator channel septum. The light from each pixel is detected by each photosensor and by amount or arrival time the active pixels can be detected.

Figure 4:
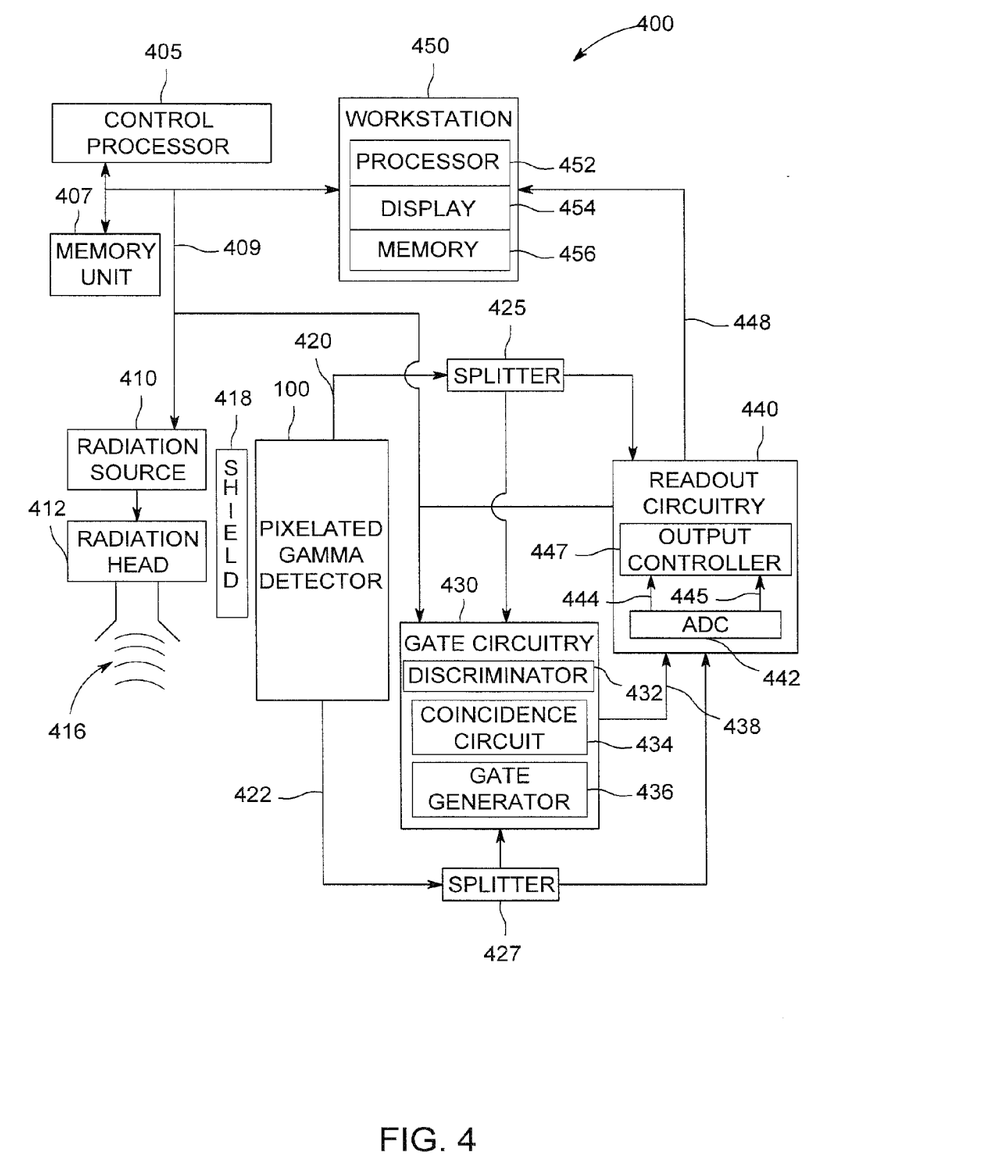
FIG. 4 depicts an inspection system incorporating the pixelated gamma detector of FIG. 1 in accordance with embodiments.

FIG. 4 depicts inspection system 400 incorporating pixelated gamma detector 100 in accordance with embodiments. Inspection system 400 can be applied to obtain inspection information and/or detection of defects in an interior of an object; particularly when the integrity of the object can only readily be accessed from its interior—e.g., boreholes, oil well, pipeline inspection, pipes, construction applications (e.g., structural elements of buildings and bridges), etc. Inspection system 400 can operate under the control of control processor 405, which is in communication with other components of borehole inspection system 400 over electronic communication network 409.

Electronic communication network 409 can be, can comprise, or can be part of, an internal data bus, a private internet protocol (IP) network, the Internet, an integrated services digital network (ISDN), frame relay connections, a modem connected to a phone line, a public switched telephone network (PSTN), a public or private data network, a local area network (LAN), a metropolitan area network (MAN), a wide area network (WAN), a wireline or wireless network, a local, regional, or global communication network, an enterprise intranet, any combination of the preceding, and/or any other suitable communication means. It should be recognized that techniques and systems disclosed herein are not limited by the nature of network 409.

Connected to control processor 405 is memory unit 407. The memory unit can contain random access memory and/or read only memory, and can be formed from volatile and non-volatile memory. Within memory unit 407 executable instructions can be stored that instruct control processor 405 to control methods and operations disclosed herein.

Inspection system 400 includes radiation source 410 that emits gamma rays or x-rays 416. Radiation source 410 can be a gamma ray source that emits gammy ray radiation—including, but not limited to, radioactive isotopes of barium, cesium, linear accelerator (LINAC) x-ray source, or combinations thereof. In some implementations radiation source 410 can include a remote radiation head 412 to emit the gamma rays or x-rays. Shield 418 can absorb direct radiation from radiation source 410. The shield can collimate or otherwise limit the emission of radiation from the source.

[is this section needed? It seems a repeat of sections before] As disclosed above, pixelated gamma detector 100 can include collimator 110 with about parallel longitudinal walls separated by about parallel collimator septum 114, which define a respective collimator channel 118. Scintillator crystals 120 are positioned abutting the respective collimator channels. Optical transparent elements 125 alternate with the scintillator crystals and are located in regions that are shadowed by the collimator septum. Scintillation light generated by scintillator crystals 120 can propagate through the column assembly to photosensors 150, 155 connected to scintillator column assembly 140 at opposing ends of the column.

Radiation source 410, pixelated gamma detector 100, and shield 418 are placed within an object to be inspected (e.g., a borehole, pipeline, pipe, etc.). Shield 418 can be positioned between the radiation source and pixelated gamma detector 100. These components can be translated along a longitudinal path within the object so as to inspect a larger area. The shield can absorb direct radiation from the source, and pixelated gamma detector 100 receives incident backscatter radiation from the object under inspection.

Pulses (TopPhS and BottomPhS) 420, 422 produced by the photosensors at either end of scintillator column assembly 140 are split into two signals by splitters 425, 427. One split signal output from each splitter is provided to gate circuitry 430. The other split signal output from each splitter is provided to readout circuitry 440.

Gate circuitry 430 can include discriminator 432 (e.g., a leading edge discriminator) that detects whether a received signal is above a predetermined threshold level. If a signal is above the threshold level, the discriminator provides a signal to timing coincidence circuit 434, which is configured to reject spurious pulses from PMTs or electronics noise. Gate generator 436 generates gate signal 438 which is provided to readout circuitry 440.

The input signals to readout circuitry 440 are digitized independently by charge-sensitive analog-to-digital convertor (ADC) 442, which has an input channel for TopPhS signal and an input channel for the BottomPhS signal. The pulses at respective input channels of the ADC are gated by gate signal 438 to reject the spurious pulses. A comparison of digitized signals 444, 445 from the photosensors by output controller 447 enables a determination of the light sharing between the two ends of the detector stack, which in turn allows measurement of the relative position x of radiation event.

Workstation 450 can receive readout circuitry output signal 448, which is representative of the inspection and/or detection result(s) of the object. The workstation can include processor 452, memory 456, and display section 454. The workstation can process output signal 448 to create image data of the integrity of the interior of the object undergoing inspection. This image data can be in graphic and/or tabular form presented by the display section (which can include a monitor, a printer, or both). For example, defects in the object can be determined by analyzing the backscatter radiation received as the devices traverse the longitudinal path (where the radiation reaching the detector differs in the presence of a defect in the object).

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

We claim:

1. A pixelated gamma detector comprising:
    a scintillator column assembly having scintillator crystals and optical transparent elements alternating along a longitudinal axis of the scintillator column;
    a collimator assembly having about parallel longitudinal walls, the longitudinal walls separated by about parallel collimator septum, the collimator septum spaced apart to form a plurality of collimator channels;
    respective ones of the scintillator crystals having a first height and width about equal in dimension to a corresponding dimension of the collimator channel;
    respective ones of the optical transparent element having a second height and width about equal in dimension to a corresponding dimension of the collimator septum;
    the scintillator column assembly positioned adjacent to the collimator assembly so that the respective ones of the scintillator crystal are positioned adjacent to respective ones of the collimator channels, and the respective ones of the optical transparent element are positioned adjacent to respective ones of the collimator septum; and
    a first photosensor and a second photosensor, the first and the second photosensor each connected to an opposing end of the scintillator column assembly.

2. The pixelated gamma detector of claim 1, including the respective optical transparent elements formed from at least one of glass, acrylic, optical epoxy, and a gas.

3. The pixelated gamma detector of claim 1, including the respective scintillator crystals formed from at least one of sodium iodide: thallium, lutetium oxy-orthosilicate, lutetium yttrium oxy-orthosilicate, bismuth germanium oxide, cerium bromide, lanthanum bromide, and gadolinium pyrosilicate.

4. The pixelated gamma detector of claim 1, including the scintillator column assembly encased in an optical transparent casing.

5. The pixelated gamma detector of claim 4, the optical transparent casing formed from at least one of clear quartz, glass, optically transparent epoxy, optical liquid, and a gas.

6. The pixelated gamma detector of claim 1, including one or more of the respective transparent elements having a different directional optical reflectivity property.

7. An inspection system for inspection of an object interior, the system comprising:
  a radiation source, a radiation shield, and a pixelated gamma detector;
  a control processor connected to an electronic communication network, the control processor in communication with the radiation source and the pixelated gamma detector across the electronic communication network;
  the radiation source, the radiation shield, and the pixelated gamma detector configured to be inserted into the object interior, and configured to be translated along a longitudinal axis of the object;
  the radiation source configured to emit gamma rays or x-rays, the shield located in proximity to the radiation source and configured to absorb a portion of direct radiation; and
  the pixelated gamma detector configured to receive backscatter radiation off the object interior, the pixelated gamma detector including:
    a scintillator column assembly having scintillator crystals and optical transparent elements alternating along a longitudinal axis of the scintillator column;
    a collimator assembly having about parallel longitudinal walls, the longitudinal walls separated by about parallel collimator septum, the collimator septum spaced apart to form a plurality of collimator channels;
    respective ones of the scintillator crystals having a first height and width about equal in dimension to a corresponding dimension of the collimator channel;
    respective ones of the optical transparent element having a second height and width about equal in dimension to a corresponding dimension of the collimator septum;
    the scintillator column assembly positioned adjacent to the collimator assembly so that the respective ones of the scintillator crystal are positioned adjacent to respective ones of the collimator channels, and the respective ones of the optical transparent element are positioned adjacent to respective ones of the collimator septum;
    a first photosensor and a second photosensor, the first and the second photosensor each connected to an opposing end of the scintillator column assembly; and
    the scintillator column assembly encased in an optical transparent casing.

8. The system of claim 7, including:
  a first signal output from the first photosensor and a second signal output from the second photosensor;
  the first and the second signal outputs connected to a respective signal splitter, each respective signal splitter configured to provide an output signal to a gate circuit and to a readout circuit.

9. The system of claim 8, including the gate circuit configured to provide a gate signal to the readout circuit.

10. The system of claim 8, the readout circuit including an analog-to-digital convertor configured to digitize each respective output signal of the splitter.

11. The system of claim 9, the readout circuit including an analog-to-digital convertor configured to digitize each respective output signal of the splitter, the digitization of each respective output signal occurring under control by the gate signal.

12. The system of claim 8, the readout circuit including an output controller configured to compare the respective digitized output signals to determine the relative position x of radiation event.

13. The system of claim 7, including a workstation configured to:
  analyze data of relative position x of radiation events provided by the readout circuitry, and backscatter radiation based on the relative position x; and
  display data representative of defects in the object interior.

14. A method for inspection of an object interior, the method comprising:
  inserting a radiation source, a radiation shield, and a pixelated gamma detector into the object interior, the radiation source emitting gamma rays or x-rays, the shield located in proximity to the radiation source and absorbing a portion of direct radiation;
  translating the radiation source, the radiation shield, and the pixelated gamma detector along a longitudinal axis of the object;
  the pixelated gamma detector receiving backscatter radiation off the object interior, the pixelated gamma detector including:
    a scintillator column assembly having scintillator crystals and optical transparent elements alternating along a longitudinal axis of the scintillator column;
    a collimator assembly having about parallel longitudinal walls, the longitudinal walls separated by about parallel collimator septum, the collimator septum spaced apart to form a plurality of collimator channels;
    respective ones of the scintillator crystals having a first height and width about equal in dimension to a corresponding dimension of the collimator channel;
    respective ones of the optical transparent element having a second height and width about equal in dimension to a corresponding dimension of the collimator septum;
    the scintillator column assembly positioned adjacent to the collimator assembly so that the respective ones of the scintillator crystal are positioned adjacent to respective ones of the collimator channels, and the respective ones of the optical transparent element are positioned adjacent to respective ones of the collimator septum;
    a first photosensor and a second photosensor, the first and the second photosensor each connected to an opposing end of the scintillator column assembly; and
    the scintillator column assembly encased in an optical transparent casing.

15. The method of claim 14, including:
the first photosensor providing a first signal output to a first signal splitter, and the second photosensor providing a second signal output to a second signal splitter;
the first and the second signal splitter each providing a respective output signal to a gate circuit and to a readout circuit.

16. The method of claim 15, including the gate circuit providing a gate signal to the readout circuit.

17. The method of claim 15, including within the readout circuitry an analog-to-digital converter digitizing a respective output signal of the splitter.

18. The method of claim 16, including within the readout circuitry an analog-to-digital convertor digitizing each respective output signal of the splitter, the digitization of each respective output signal occurring under control by the gate signal.

19. The method of claim 15, including within the readout circuitry an output controller comparing the respective digitized output signals to determine the relative position x of radiation events of the backscatter radiation.

20. The method of claim 14, including a workstation analyzing the relative position x of radiation events data provided by the readout circuitry, and backscatter radiation based on the relative position x determined backscatter radiation; and
displaying data representative of defects in the object interior.

* * * * *